United States Patent [19]
Oh

[11] Patent Number: 5,904,824
[45] Date of Patent: May 18, 1999

[54] MICROFLUIDIC ELECTROPHORESIS DEVICE

[75] Inventor: Chan S. Oh, Chino Hills, Calif.

[73] Assignee: Beckman Instruments, Inc., Fullerton, Calif.

[21] Appl. No.: 08/814,755

[22] Filed: Mar. 7, 1997

[51] Int. Cl.$^6$ .................................................. C25B 7/00
[52] U.S. Cl. .......................................... 204/601; 204/600
[58] Field of Search ................................ 204/450, 451, 204/454, 548, 600, 601, 641; 422/56, 57, 58, 100, 102; 436/180; 435/288.3, 288.4; 210/656, 658, 198.2, 198.3

[56] References Cited

U.S. PATENT DOCUMENTS

| | | | |
|---|---|---|---|
| 4,124,470 | 11/1978 | Dahms | 204/450 |
| 4,233,029 | 11/1980 | Columbus | 422/400 |
| 4,747,919 | 5/1988 | Anderson | 204/455 |
| 4,997,537 | 3/1991 | Karger et al. | 204/453 |
| 5,045,172 | 9/1991 | Guzman | 204/452 |
| 5,312,535 | 5/1994 | Waska et al. | 204/603 |
| 5,413,686 | 5/1995 | Klein et al. | 204/603 |
| 5,447,617 | 9/1995 | Shieh | 204/601 |
| 5,470,739 | 11/1995 | Akaike et al. | 435/402 |

FOREIGN PATENT DOCUMENTS 0339779  11/1989  European Pat. Off. .

OTHER PUBLICATIONS

Kuhn et al., "Capillary Electrophoresis: Principles and Practice", p. 122, 1993.

*Primary Examiner*—William H. Beisner
*Assistant Examiner*—Theresa T. Snider
*Attorney, Agent, or Firm*—William H. May; P. R. Harder; Sheldon & Mak

[57] ABSTRACT

A microfluidic device having opposed spaced apart sheets of siliceous material, such as glass, the opposed facing sides of each of the sheets having hydrophilic and hydrophobic areas which form therebetween a fluid capillary which is hydrophilic and bounded by hydrophobic areas to form an microfluidic hydrophilic fluid pathway. The preferred device is useful for capillary electrophoresis.

15 Claims, 1 Drawing Sheet

MICROFLUIDIC ELECTROPHORESIS DEVICE

BACKGROUND OF INVENTION

The value of electrophoresis in clinical chemistry has been recognized for some time in the analysis of proteins in body fluids. Gel electrophoresis is the older method used in clinical chemistry laboratories. With gel electrophoresis, a sample is applied near one edge of a layer of gelatin carried on a flexible sheet slab of gel. The gel is electrophoresised, stained and the density of the resulting pattern is measured to reveal the sample such as proteins and nucleic acids. Although gel electrophoresis is relatively inexpensive in terms of the supplies and equipment required to perform sample analyses, the technique requires skilled technicians and is time consuming, effectively resulting in a high price per test and limiting the number of tests that can be performed using the technique.

Efforts have been made to improve electrophoresis in the clinical laboratory. For example, U.S. Pat. No. 4,124,470 to Dahms describes a zone electrophoresis apparatus where a number of samples in individual large-bore tubes can be processed serially on a turntable.

Capillary electrophoresis is a more recent development. In capillary electrophoresis, a small tube or capillary having an inside bore diameter in the range of about five microns to about two hundred microns and often about twenty cm long is filled with an electrically conductive fluid, or buffer. A direct current voltage in a range of about 2,000 volts to about 30,000 volts is applied to the ends of the capillary by means of electrodes positioned in the buffer reservoirs, causing a small current, typically in the range of about five microamps to about one milliamp, to flow through the capillary.

With the correct polarity applied across the capillary, the sample begins to migrate from the sample introduction end toward the other end of the capillary. As this migration occurs, different molecules in the sample travel at different rates primarily because of slightly different electrical charges on the molecules. These different migration rates cause molecules with slightly different charges to separate one from the other, some moving more quickly and advancing relatively with respect to more slowly moving molecules. As the sample nears the other end of the capillary, the small volume of sample becomes separated into bands of different molecules according to the relative migration rates of the molecules. These bands or groups of different molecules are detected near the other end of the capillary by, for example, passing a light beam through the bore of the capillary. Changes to the light beam, such as absorbance caused by the different molecules, are detected as the separated molecules pass through the beam, thus identifying the different molecules or the classes or categories of molecules in the sample and the relative concentration of such molecules.

The core of each capillary electrophoresis system is the capillary. Although there are capillaries made of borosilicate glass or Teflon, fused silica is by far the most frequently used material. This is owing to the intrinsic properties of fused silica like the superior transparency for UV light, the high thermal conductance and the feasibility of manufacturing capillaries with diameters of a few micrometers. Because bare fused silica capillaries are extremely fragile, they are externally coated with a polyimide polymer to improve the flexibility and to make handling easier. However, a small amount of the polyimide coating has to be removed to allow light passage for detection.

Capillary electrophoresis analyzers using small bore tubes are known in the art. For example, in European Patent Application Number 89302489.3, Publication Number 0,339,779 A2, the ends of the capillaries along with electrodes are inserted into the vials by means of hypodermics that pierce caps on the vials. A single detector provides detection of electrophoresised samples.

Another automated capillary electrophoresis apparatus is described in U.S. Pat. No. 5,045,172 to Guzman. A capillary, which is described in Guzman as being a single capillary or a plurality of capillary tubes operated in parallel or in a bundle, has two opposite ends. Other small bore tube capillary electrophoresis devices are described in Klein, U.S. Pat. No. 5,413,686 and Waska et al, U.S. Pat. No. 5,312,535.

As an alternative to the cylindrical capillary glass tubes, rectangular capillaries have been disclosed by Tsuda et al, "Rectangular Capillaries for Capillary Zone Electrophoresis", Anal. Chem. 62 (1990) 2149–2152. Some of the advantages of these systems are their efficient heat dissipation due to the large height-to-width ratio and, hence, their high surface-to-volume ratio and their high detection sensitivity for optical on-column detection modes. According to the authors, these flat separation channels have the ability to perform two-dimensional separations, with one force being applied across the separation channel, and with the sample zones detected by the use of a multi-channel array detector. A significant disadvantage of rectangular capillaries are their thin walls, equal to the width of the narrowest dimension; for instance 20 um for 20×20 $um^2$ capillaries. Special care must be taken to avoid breakage of these capillaries. The rectangular as well as circular capillaries of the prior art do not allow multiple electrodes or detectors at any one or more desired points between the ends of the fluid pathway.

The present invention provides a novel microfluidic device useful in capillary electrophoresis analyzers and other fluidic devices for separation and analysis of proteins, nucleic acids and other chemical compounds.

SUMMARY OF INVENTION

The present invention includes the following:

(1) A microfluidic device comprising opposed spaced apart sheets of hydrated oxide material such as a siliceous material, the opposed facing sides of each of said sheets having hydrophilic and hydrophobic areas which form therebetween a fluid capillary which is hydrophilic and bounded by hydrophobic areas to form at least one microfluidic hydrophilic fluid pathway.

(2) A capillary electrophoresis device comprising opposed spaced apart sheets of siliceous material, the opposed facing sides of each of said sheets having hydrophilic and hydrophobic areas which form therebetween a fluid capillary which is hydrophilic and bounded by hydrophobic areas to form at least one electrophoretic hydrophilic fluid pathway.

(3) In an automated capillary electrophoresis apparatus comprising at least one fluid capillary; the improvement wherein said capillary is in the form of opposed spaced apart sheets of siliceous material, the opposed facing sides of each of said sheets having hydrophilic and hydrophobic areas which form therebetween a fluid capillary which is hydrophilic and bounded by hydrophobic areas to form at least one electrophoretic hydrophilic fluid pathway.

(4) The method of confining aqueous solution on flat glass (siliceous materials, i.e. quartz, soda, or lead glasses) by forming two siliceous sheets each of which have facing sides containing hydrophilic and hydrophobic areas, and opposing the facing sides of each of said sheets to form therebetween a fluid capillary which is hydrophilic and bounded by hydrophobic areas adapted to provide at least one hydrophilic fluid pathway.

DESCRIPTION OF PREFERRED EMBODIMENTS

The surface of siliceous materials such as glass are naturally hydrophilic due to the presence of multiple hydroxyl groups which are attached to the tetravalent silicone atoms of the glass. According to this invention, these hydroxyl groups can undergo a dehydration reaction with an alkyl-chlorosilane or alkyl-alkoxysilane in a suitable anhydrous organic solvent to render the treated area hydrophobic. The silanol moiety of the glass forms a covalent with an organic monohalo silane such as a trialkyl chloro silane or a alkyl-trialkoxy silane compound via an Si-O-Si bond. Thus, the surface properties of a glass substrate are modified by the alkylsilane group. Various silane derivatives, which are commercially available, are suitable for the practice of this invention. The organic monohalo silanes have the general formula: (a) and alkyltrialkoxysilanes (b)

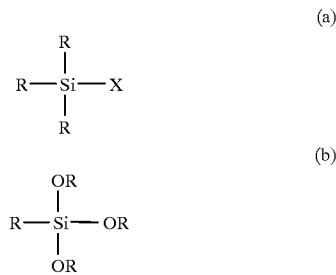

wherein the R groups are alkyl or alkoxy such as methyl, dodecyl, octadecyl and the like, and X is a halogen, preferably chlorine. Typically, the alkyl or alkoxy groups on the silanes contain from 1 to about 30 carbon atoms. For example, octadecyl-dimethylchlorosilane is useful to produce the hydrophobic areas on the siliceous surfaces according to this invention. The silanizing agent can be dissolved in toluene or other solvent. The solution can be applied to the siliceous areas to be rendered hydrophobic by roller or printing head and heated to evaporate the solvent. Any, excess silanizing agent can be removed by washing with fresh organic solvents.

A glass surface having such "hydrophobic" (water repelling) regions in a predetermined pattern can be obtained by the use of a silane resistant mask. The areas covered by the mask are shielded from the silane. Only the areas exposed to the silane are rendered hydrophobic. This results in an anisotropic surface on a single substrate. In other words, a single glass substrate contains hydrophobic and hydrophilic regions in a pre-determined pattern. When an aqueous solution is subsequently applied on top of such an anisotropic surface, the aqueous solution will "wet" (adhere to) the surface in the pre-determined pattern. In a particular pattern, such hydrophobic surface can be formed all over the glass surface except a narrow gap which defines a hydrophilic channel. When two such anisotropic substrates thus prepared with mirror image hydrophilic and hydrophobic regions are placed in superposed position with thin edge spacers or shims therebetween and having the hydrophilic channel of the top and bottom substrates face-to-face, a microfluidic device having a hydrophilic fluid pathway is formed.

The spacing between the top and bottom siliceous substrates can be maintained by use of appropriate spacers or shims of any desired composition and the edges of the two substrates can be sealed to maintain the physical stability.

For example, the spacers between the facing substrates can be Mylar (polyester sheet of Dupont) shims of known thickness at the lateral edges of the substrates. For permanency, epoxy resin adhesive preferably can be applied to the shims to secure the substrates together. The composition of the shims is not in any sense critical. In general, any adhesive capable of bonding to siliceous materials can be used to hold the shims in place. There is obtained a "channel" of hydrophilic glass surface on the two facing sides and the rest of the top and bottom glasses are composed of hydrophobic surface. The gap or spacing between the two superposed flat glass sheets is preferably from about 25 to about 200 microns and more preferably about 50 to about 100 microns. The fluid pathway channel is a capillary in the form of a long rectangular tube with two surfaces being hydrophilic glass and the other two sides are air. When an aqueous Tris buffer solution used in capillary electrophoresis is contacted with one end of the rectangular capillary, it travels and fills the whole length of the capillary. The buffer solution is observed to form a long rectangular tube confined by the two glass substrates and two air walls. The aqueous solution does not wet the hydrophobic areas.

One alternative method of patterning a hydrophobic surface on any hydrated oxide surface including silica or glass involves applying a chemical by dip coating or spin coating. In this case, the chemical used renders the entire surface hydrophobic. The coated substrate can be subsequently baked, if necessary. Ultraviolet light exposure through a photo-mask or any other photo-resist technique, of certain desired area or pattern, will render the area exposed to ultraviolet "hydrophilic".

A suitable photo-sensitive chemical is based on 3-amino-propyl-trimethoxy-silane. A preferred photo-sensitive chemical is obtained by reacting the NHS-ester of polyethyleneoxide half acid with 3-amino-propyl-trimethoxy silane. The other carboxylic acid group is then reacted (after converting to primary amino terminus by treating with ethylene-diamine) with octadecyloxy-o-nitrobenzoic acid to obtain the following photo silane compound:

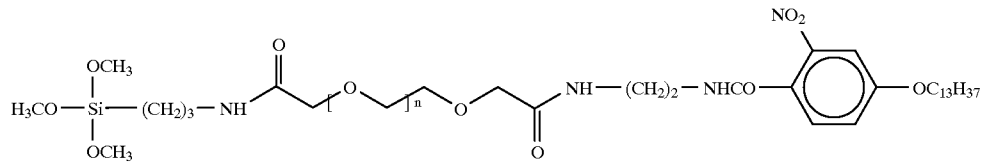

This compound, when contacted with a siliceous surface, renders the surface hydrophobic.

This compound will decompose to form hydrophilic area on the siliceous substrate upon exposure to 360 nm UV light as follows:

PHOTO-SILANE

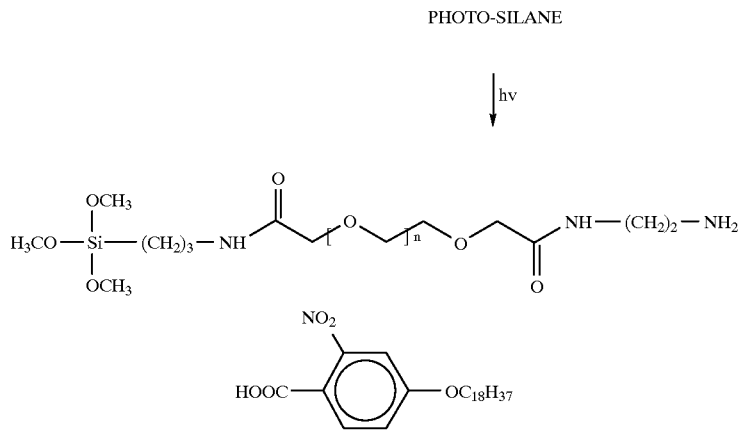

The o-Nitrobenzoic acid decomposes via the well known mechanism. By washing the excess materials from the surface with appropriate "organic solvent", an "anisotropic (horizontally)" surface is obtained.

Thus, when a siliceous surface is coated with the photo silane compound, the entire surface is rendered hydrophobic. Then, a mask made of any material which does not transmit ultraviolet is applied, covering only the areas desired to remain hydrophobic. The coated siliceous surface is exposed to ultraviolet and the photo-silane decomposes to yield a hydrophilic surface in the exposed areas. A complete electrophoresis or other microfluidic cell can be built up from two siliceous substrates processed in this way.

In addition to forming the hydrophilic areas, it is contemplated that electrodes or a plurality of electrodes will be deposited on one or both glass substrates. The electrodes can be deposited by sputtering or photo defined involving known techniques. The electrodes can be positioned to be generally perpendicular to the capillary length (or hydrophobic-hydrophilic channel length). An electric field can be applied to these electrodes which will create an electric field manipulated from outside the capillary. The "micro-electric field" can be programmed for varying amplitudes, time duration and timing sequence. Also the polarity of such electric field can be reversed with varying amplitudes, duration, repetition or sequence during the course of electrophoretic procedures. Many beneficial results are obtained using such device for better separation, shorter separation time and lower operating voltages.

It is also intended to install "on-line" chemical sensors inside the capillary tube, and also multiples of different chemical sensors in the same device. Many beneficial results can be obtained using such "in-line" chemical sensors for better detection sensitivity and selectivity or otherwise impossible detection during capillary electrophoresis, or any other microfluidics apparatus.

As many electrodes and sensors as desired can be established along the fluid pathway.

The present invention by providing a "flattened capillary" simplifies the optics used for capillary electrophoresis and other microfluidics. The channel or fluid pathway width can vary to any width or shape using any of the procedures discussed herein.

THE DRAWINGS

Turning to the drawings.

Figure 1:
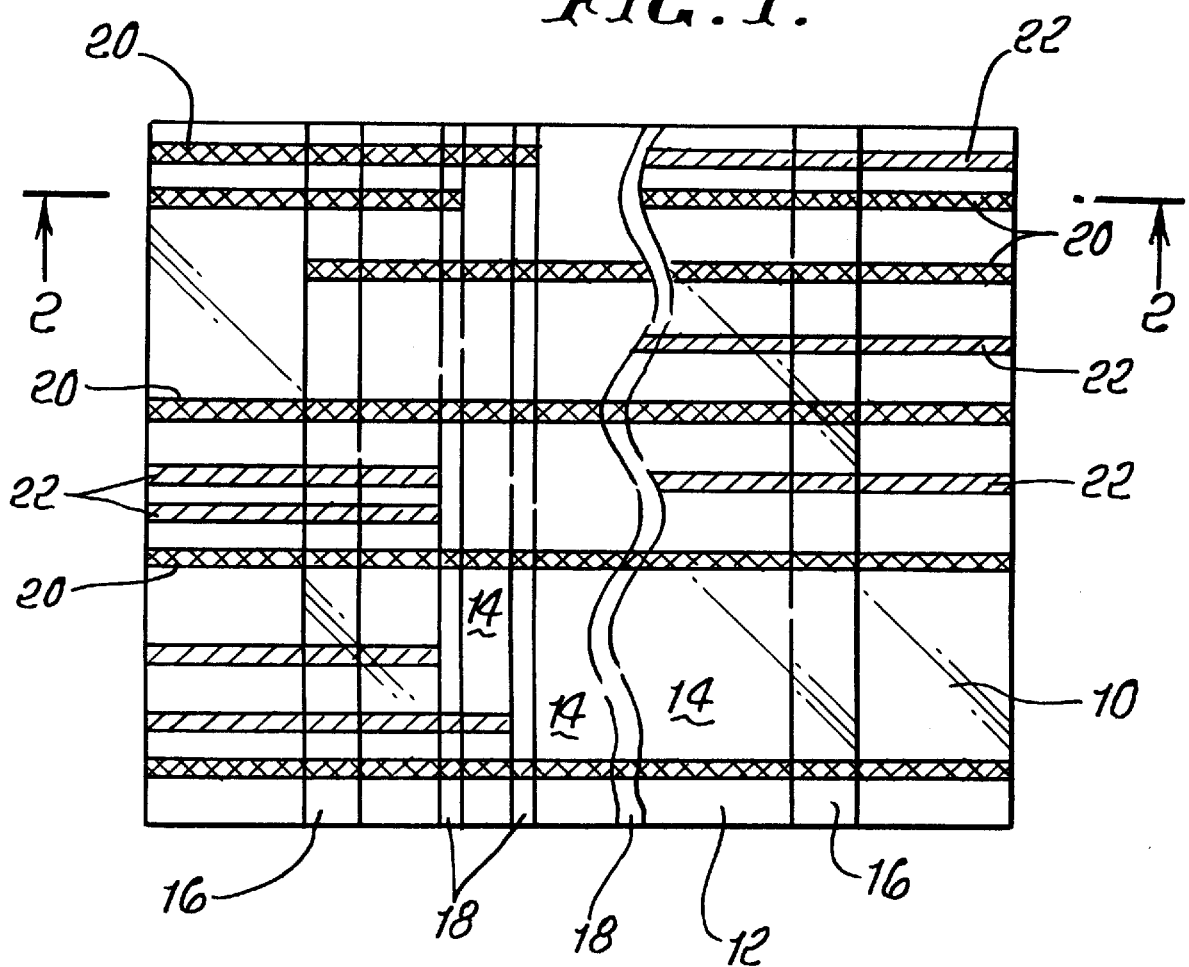
FIG. 1 is a top view of an embodiment of this invention looking through the top transparent layer.
Figure 2:
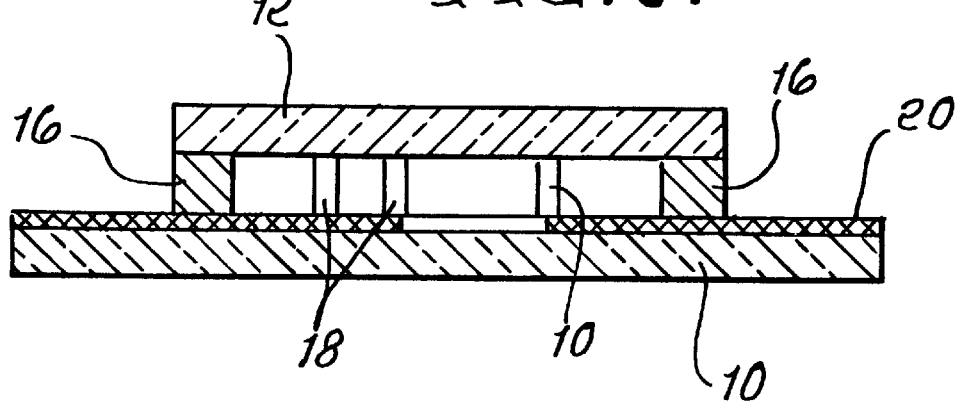
FIG. 2 is a sectional view of the apparatus of FIG. 1 taken along the line 2—2 in FIG. 1.

In the drawings, the lower siliceous glass layer is 10 and the upper siliceous glass layer is 12. The hydrophobic areas are indicated by the numeral 14, the adhesive separators or spacers are 16. The hydrophilic areas forming electrophoretic channels are 18.

The electrodes are 20 and the sensors or other detectors are 22.

The electrophoretic channel or pathway, as indicated by the drawings, can be straight, curved, sinuous, etc. In general, the width of the hydrophobic area forming the channel is from about 5 microns to about 200 microns in width.

EXAMPLE I

A microscope slide glass was marked with lines with a Q-tip impregnated with a toluene solution of octadecyl dimethyl-chlorosilane. The glass was air dried. Water was applied to the treated surface of the glass slide. The water did not wet the areas where the octadecyl dimethyl-chlorosilane was deposited. The visible excess material from the slide was rubbed off with Kimwipe and added water again. The water again remembered where the previously marked areas were, which indicated the invisible but definite presence of hydrophobic areas, indicating that the chloro-part of the silane compound bonded to the glass surface.

Two such microscope glasses were prepared which had been previously "scored" or marked by a pair of parallel hydrophobic lines separated by 50 microns. When the two glass sheets are mated in such a manner that the hydrophobic lines of both glass sheets are lined up and the sheets separated by epoxy adhesive shims at the side edges to the sheets, a hydrophilic "channel" is defined between the two hydrophobic lines of the opposite glass sheets (top and bottom), and between the two parallel hydrophobic lines on each of the top and bottom glass sheets. When an aqueous solution is introduced between the glass sheets, the liquid forms a long line in the shape of a rectangular tube in the hydrophilic channel. The aqueous solution stays within the boundary defined by the hydrophobic lines and maintains intimate contact with the top and bottom glass surfaces. High voltage can be applied between the two ends of the hydrophilic channel and cause the liquid movement.

EXAMPLE II

Glass Microscope Slide Glass was tested for water sheeting. Water sheeted uniformly from top to bottom. Non-sticking Scotch Tape was attached to the glass and removed. Water sheeting test was repeated. Water sheeted again uniformly which established that nothing in the Scotch tape alters the hydrophilic groups on the surface of the glass. The Scotch tape was cut about 5 mm width and covered the entire length of the glass in the area in which it is desired to maintain the hydrophilic property. Applying pressure to the top of the Tape made the adhesion uniform. A second glass slide was prepared the same as the first glass. A spray bottle was filled with a solution of octadecyl-dimethylchlorosilane dissolved in toluene (about 3 grams in 150 ml toluene). The above two pieces of glass were sprayed with the contents of the spray bottle. The sprayed surfaces appeared foggy indicating copious amounts of material deposited. After washing with water, the tapes were removed. The glass surfaces underneath the tapes remained clear. A spacer, ¼ inch width, 4 inches long pieces of 2×25 (two, one on top of the other) micron Mylar was prepared and carefully placed at each of the long side edges of the bottom glass. Each side had two shims, giving a layer having a total thickness of about 50 microns. The top glass was carefully placed on top of the bottom glass, the clear hydrophilic channels of the top glass and bottom glasses were aligned. Clamps were attached at the four corners of the assembly. Thus, a hydrophilic chamber of about 5 mm×75 mm×50 microns was obtained. An aqueous solution of a dye was applied at the one end of the channel. The dyed solution rapidly moved through the channel by capillary action. The channel definition marked by the edges of the hydrophobic silane treated area was clearly visible. The cell (assembly) was disassembled and washed with water. After drying with air, the cell was reassembled. The dye solution again faithfully filled the hydrophilic channel as before. A cell with about 2 mm channel width was similarly assembled and without any observable difficulty the dye solution filled the channel.

The cell was disassembled, washed and air blown dried. The glasses were reassembled. A metal plate about 1 inch square was attached to wire and placed on top of a rubber block. On top of the metal plate was placed about 0.75 inch square Whatman filter paper. The filter paper was added with a few drops of Borate buffer (100 mM, pH 10.6) and the cell assembly was placed on top of the wet filter paper. The bottom side of the cell had shorter piece of the Microscope slide glass and the top piece protruded beyond the bottom piece in such a manner that the assembly rested on the wetted filter paper-metal-rubber block. The buffer solution spontaneously filled the hydrophilic channel all the way to the other extreme of the channel. The other side of the cell assembly had the bottom piece protruding beyond the top shorter piece. The filter paper was placed on top of the bottom piece and the other metal electrode piece was placed on top of the wet filter paper. The two metal electrodes were connected to the power source. A few microliters of aqueous dye solution was placed at the entrance to the channel on the side of the assembly were the bottom glass was longer and facing upward. Immediately the power was turned on to about 485 volts and the monitored current gradually increased from about 200 microamps to 1 milliamp (after about 15 minutes run). The dye migrated toward the opposite electrode as anticipated.

Having fully defined the invention, it is intended that it be limited only by the lawful scope of the following claims.

I claim:

1. A microfluidic device comprising opposed spaced apart sheets of hydrated oxide material, the opposed facing sides of each of said sheets having hydrophilic and hydrophobic areas which form therebetween a fluid capillary which is hydrophilic and bounded by hydrophobic areas to form at least one microfluidic hydrophilic fluid pathway.

2. The microfluidic device of claim 1 wherein said fluid pathway is generally square or rectangular in cross section.

3. The microfluidic device of claim 1 wherein electrodes and chemical sensors are provided between the spaced apart sheets and in communication with said fluid pathway.

4. The microfluidic device of claim 3 wherein the electrodes and chemical sensors are generally at about right angles to the general direction of fluid movement in the fluid pathway.

5. A microfluidic capillary electrophoresis device comprising opposed spaced apart sheets of siliceous material, the opposed facing sides of each of said sheets having hydrophilic and hydrophobic areas which form therebetween a fluid capillary which is hydrophilic and bounded by hydrophobic areas to form at least one electrophoretic hydrophilic fluid pathway.

6. The device of claim 5, wherein the siliceous material is glass.

7. A capillary electrophoresis device comprising opposed spaced apart glass sheets, the opposed facing sides of each of said sheets having hydrophilic and hydrophobic areas which form therebetween a fluid capillary which is hydrophilic and bounded by hydrophobic areas to form an electrophoretic hydrophilic fluid pathway.

8. In an automated capillary electrophoresis apparatus comprising at least one fluid capillary; the improvement wherein said capillary is in the form of opposed spaced apart sheets of hydrated oxide material, the opposed facing sides of each of said sheets having hydrophilic and hydrophobic areas which form therebetween a fluid capillary which is hydrophilic and bounded by hydrophobic areas to form an electrophoretic hydrophilic fluid pathway.

9. A capillary electrophoresis device comprising opposed spaced apart sheets of hydrated oxide material, the opposed facing sides of each of said sheets having hydrophilic and hydrophobic areas which form therebetween a fluid capillary which is hydrophilic and bounded by hydrophobic areas to form an electrophoretic hydrophilic fluid pathway.

10. The capillary electrophoresis device of claim 9 wherein said fluid pathway is generally square or rectangular in cross section.

11. The capillary electrophoresis device of claim 9 wherein electrodes and chemical sensors are provided between the spaced apart sheets and in communication with a fluid pathway.

12. The capillary electrophoresis device of claim 11 wherein the electrodes and chemical sensors are generally at about right angles to the general direction of fluid movement in the fluid pathway.

13. The capillary electrophoresis device of claim 9 wherein the hydrophobic areas are formed by reaction of the siliceous material with an organic monohalo silane.

14. The device of claim 9 wherein the sheets are maintained in spaced apart relationship by spacers adhered to said sheets.

15. The device of claim 9 wherein the spacing between sheets is from about 25 to about 200 microns.

* * * * *